United States Patent [19]
Nilsen et al.

[11] Patent Number: 5,885,594
[45] Date of Patent: Mar. 23, 1999

[54] ORAL COMPOSITIONS HAVING ENHANCED MOUTH-FEEL

[75] Inventors: Stephen James Nilsen, Cincinnati; Gary Lyle Walden, West Chester, both of Ohio

[73] Assignee: The Procter & Gamble Company, Cincinnati, Ohio

[21] Appl. No.: 825,041

[22] Filed: Mar. 27, 1997

[51] Int. Cl.$^6$ ................................................ A61K 7/00
[52] U.S. Cl. ................................ 424/401; 424/49; 424/57
[58] Field of Search ................................ 424/401, 49, 57

[56] References Cited

U.S. PATENT DOCUMENTS

| | | | |
|---|---|---|---|
| 4,097,604 | 6/1978 | Thiele | 424/318 |
| 4,199,608 | 4/1980 | Gilmore | 426/570 |
| 4,214,006 | 7/1980 | Thiele | 424/318 |
| 4,215,144 | 7/1980 | Thiele | 424/318 |
| 4,284,655 | 8/1981 | Miller et al. | 426/602 |
| 4,393,043 | 7/1983 | Koulbanis et al. | 424/59 |
| 4,414,229 | 11/1983 | Bakal et al. | 426/98 |
| 4,528,197 | 7/1985 | Blackburn | 514/552 |
| 4,607,052 | 8/1986 | Mendy et al. | 514/547 |
| 4,832,975 | 5/1989 | Yang | 426/607 |
| 5,017,614 | 5/1991 | Pariza et al. | 514/558 |
| 5,070,104 | 12/1991 | Pariza et al. | 514/549 |
| 5,092,964 | 3/1992 | Conte, Jr. et al. | 203/29 |
| 5,208,356 | 5/1993 | Pariza et al. | 554/79 |
| 5,225,441 | 7/1993 | Vogel et al. | 514/557 |
| 5,258,197 | 11/1993 | Wheeler et al. | 426/607 |
| 5,378,486 | 1/1995 | Sullivan | 426/549 |
| 5,378,490 | 1/1995 | Wheeler et al. | 426/606 |
| 5,380,538 | 1/1995 | Wheeler et al. | 426/99 |
| 5,382,440 | 1/1995 | Sullivan | 426/138 |
| 5,411,756 | 5/1995 | Wheeler et al. | 426/607 |
| 5,428,072 | 6/1995 | Cook et al. | 514/560 |
| 5,430,066 | 7/1995 | Cook et al. | 514/558 |
| 5,456,939 | 10/1995 | Wheeler et al. | 426/660 |
| 5,500,361 | 3/1996 | Kinney | 435/172.3 |
| 5,530,186 | 6/1996 | Hitz | 800/205 |
| 5,552,174 | 9/1996 | Wheeler et al. | 426/607 |
| 5,554,646 | 9/1996 | Cook et al. | 514/456 |

FOREIGN PATENT DOCUMENTS

| | | | |
|---|---|---|---|
| 0732 064 A1 | 9/1996 | European Pat. Off. | A23L 1/221 |
| 0779033 HEI | 6/1997 | European Pat. Off. | A23D 9/00 |
| 6-9276939 | 10/1994 | Japan | A23D 9/00 |
| WO 95/34222 | 12/1995 | WIPO | A23L 1/23 |

OTHER PUBLICATIONS

Mirsky, S., "Chewing the Fat", Scientific American (Jan. 1997), p. 31.

Mattes, R., "Oral Fat Exposure Alters Posprandial Lipid Metabolism in Humans", American Journal of Clinical Nutrition, vol. 63 (1996), pp. 911–917.

*Primary Examiner*—Thurman K. Page
*Assistant Examiner*—D. Faulkner
*Attorney, Agent, or Firm*—Loy M. White; Douglas C. Mohl; T. David Reed

[57] ABSTRACT

The present invention relates to oral compositions having enhanced organoleptic characteristics of fattiness, creaminess, soothing, satisfaction, and full mouthfeel, and comprises acylglycerol compounds having substituents $R_1$, $R_2$, and $R_3$ attached at the positions of the $OH^{31}$ groups of a glycerol backbone. The substituents $R^1$ and $R_2$ are independently selected from conjugated polyunsaturated fatty acids having from 16 carbon atoms to 22 carbon atoms and $R_3$ is selected from the group consisting of $R_1$, OH, $PO_3HR_4$, and $C_6$–$C_{12}$ carboxylic acids, wherein $R_4$ is selected from the group consisting of OH, choline, inositol, serine, and ethanolamine. The oral compositions of the present invention being substantially free of free conjugated polyunsaturated fatty acids.

6 Claims, No Drawings

ORAL COMPOSITIONS HAVING ENHANCED MOUTH-FEEL

TECHNICAL FIELD

The present invention relates to oral compositions having enhanced organoleptic characteristics of fattiness, creaminess, soothing, satisfaction, and full mouthfeel. The oral compositions comprise specific acylglycerol compounds comprising long chain conjugated polyunsaturated fatty acid residues, preferably comprising at least one conjugated linoleic acid residue. The present invention further relates to methods for enhancing organoleptic characteristics of oral compositions comprising the addition of specific acylglycerol compounds to such compositions.

BACKGROUND

The desirability of many consumable compositions, especially in low fat or so-called "light" compositions, by the consumer depends, not only on taste, but also on mouthfeel. While the gustatory or taste notes of the compositions may be, more or less, adequately compensated for, the difficulty in reconstituting or reproducing the feeling of the creamy-type consistency or texture which are precisely imparted by fats within the compositions, still remains to be a problem.

It is known that fat is comprised of a mixture of glycerol esters and that the removal of fat from various consumable compositions can adversely affect the organoleptic characteristics of the compositions. As disclosed in U.S. Pat. No. 5,092,964, issued Mar. 3, 1992, to Conte, Jr., et al., the presence of some mono- and diglycerides in butter fat and the unique triglyceride composition make important contributions to the mouthfeel of butter. Alteration of the concentration of these components in butter fat and the relative proportions thereof yields unacceptable mouthfeel. For example, while the development of low calorie triglycerides for foods having reduced fat content, wherein the triglycerides are tailored to consist of a particular combination of saturated medium chain, saturated long chain, and unsaturated long chain fatty acid residues, such as those disclosed in U.S. Pat. No. 4,832,975, issued May 23, 1989, to Yang, and triglycerides comprising both long, saturated fatty acid residues and short, carboxylic acid residues, such as those disclosed in U.S. Pat. No. 5,552,174, issued Sep. 3, 1996, to Wheeler, et al., may provide some reduction in fat and/or calories, they are still less desirable than conventional compositions.

Other attempts to provide low fat/calorie compositions have shown similar results. For example, U.S. Pat. No. 4,199,608, issued Apr. 22, 1980, to Gilmore, et al., and U.S. Pat. No. 4,284,655, issued Aug. 18, 1981, to Miller, et al., which disclose replacing fat with a partial glycerol ester composition, comprising a mixture of mono-, di-, and triglycerides, in whippable toppings and/or comestible spreads; U.S. Pat. No. 4,414,229, issued Nov., 8, 1983, to Bakal, et al., which discloses adding cellulose fibers to butter substitute spreads; and PCT Application No. WO 9,534,222, published Dec. 21, 1995, to Benzi, et al., which discloses adding the diglyceride fraction of an animal or vegetable fat hydrolysate to the flavoring ingredient of low-fat foods.

Conjugated polyunsaturated fatty acids have been known for some time and each of the different acids possess different characteristics and functional properties. For example, conjugated linoleic acid is known to possess anti-oxidation and browning-prevention properties when added to food/food products, as disclosed by Koizumi, et al., Japanese Kokai Patent Application No. HEI 6-276939, published Oct. 4, 1994; inhibit mold growth, as disclosed by Pariza, et al., U.S. Pat. Nos. 5,017,614, issued May 21, 1991, and 5,208, 356, issued May 4, 1993; and increase the efficiency of feed conversion in an animal into body weight by increasing the ratio of lean to fat body mass, as disclosed by Cook, et al., U.S. Pat. No. 5,428,072, which issued Jun. 27, 1995. It has not been known until the present invention, however, that specific acylglycerol compounds comprising conjugated polyunsaturated acids having from 16 to 22 carbons, including conjugated linoleic acid in particular, when added to various oral compositions, including conventional, reduced fat/calorie, low fat/calorie, and no fat/calorie foods and/or beverages/drinks, dental compositions, over-the-counter and/or prescription pharmaceuticals, and nutraceuticals, which when delivered in the mouth, provide enhanced organoleptic characteristics of fattiness, creaminess, soothing, satisfaction, and full mouthfeel. Therefore, the compositions and methods of the present invention are novel.

As a result of the above described discoveries, the present invention provides at least four distinct advantages over compounds disclosed in the prior art. First, the precise acylglycerol compounds of the present invention can be obtained at high purity either by de novo synthesis or purification from natural sources; second, the compounds of the present invention can be used at levels much lower than would be required of other compounds to obtain similar attributes, and therefore provides oral compositions containing less overall fat content than those compositions comprising butterfat, glycerol esters, or fat hydrolysates; third, formulations containing the preferred identified compounds provide a method for delivering the health benefits associated with conjugated linoleic acid; and fourth, these compounds augment the oxidative stability of the compositions in which they are incorporated.

Therefore, it is an object of the present invention to disclose oral compositions having enhanced mouthfeel comprising specific acylglycerol compounds comprising conjugated polyunsaturated fatty acid residues.

It is a further object of the present invention to disclose a method for enhancing the mouthfeel of oral compositions by the addition, to said compositions, of specific acylglycerol compounds comprising conjugated polyunsaturated fatty acid residues.

SUMMARY OF THE INVENTION

The present invention comprises oral compositions, selected from the group consisting of foods, beverages, dental compositions, over-the-counter and/or prescription pharmaceuticals, and nutraceuticals. The oral compositions having enhanced mouthfeel comprise acylglycerol compounds having substituents $R_1$, $R_2$, and $R_3$ attached at the positions of the $OH^-$ groups of a glycerol backbone, wherein substituents $R_1$ and $R_2$ are independently selected from conjugated polyunsaturated fatty acids having from 16 carbon atoms to 22 carbon atoms, preferably conjugated linoleic acid, conjugated linolenic acid, and conjugated arachidonic acid, more preferably wherein at least one of $R_1$ and $R_2$ is conjugated linoleic acid, most preferably wherein $R_1$ and $R_2$ are conjugated linoleic acid; and $R_3$ is selected from the group consisting of $R_1$, OH, $PO_3HR_4$, wherein further $R_4$ is selected from the group consisting of OH, choline, inositol, serine, and ethanolamine, and $C_6$–$C_{12}$ carboxylic acids, preferably $R_1$, OH, and $C_6$–$C_{12}$ carboxylic acids, more preferably conjugated linoleic acid, OH, and $C_6$–$C_{12}$ carboxylic acids, most preferably conjugated linoleic acid and OH. The acylglycerol compounds being substantially free of free conjugated polyunsaturated fatty acids.

The oral compositions of the present invention further comprise a mixture of said acylglycerol compounds, wherein said mixture comprises from about 0% to about 100%, preferably from about 50% to about 100%, more preferably from about 70% to about 100%, most preferably from about 90% to about 100% acylglycerol compounds wherein $R_1$ and $R_2$ are conjugated polyunsaturated fatty acids, preferably conjugated linoleic acid, and $R_3$ is selected from the group consisting of OH and $C_6$–$C_{12}$ carboxylic acids, or in the alternative, wherein $R_1$, $R_2$, and $R_3$ are conjugated polyunsaturated fatty acids, preferably conjugated linoleic acid; and from about 100% to about 0%, preferably from about 50% to about 0%, more preferably from about 30% to about 0%, most preferably from about 10% to about 0% acylglycerol compounds wherein $R_1$, $R_2$, and $R_3$ are conjugated polyunsaturated fatty acids, preferably conjugated linoleic acid, or in the alternative, wherein $R_1$ and $R_2$ are conjugated polyunsaturated fatty acids, preferably conjugated linoleic acid, and $R_3$ is selected from the group consisting of OH and $C_6$–$C_{12}$ carboxylic acids.

The oral compositions of the present invention still further comprise acylglycerol compounds wherein one of $R_1$ and $R_2$ is palmitic acid, preferably wherein $R_1$ is conjugated linoleic acid, conjugated linolenic acid, and conjugated arachidonic acid, more preferably wherein $R_1$ is conjugated linoleic acid.

The oral compositions of the present invention even still further comprise acylglycerol compounds wherein $R_1$ and $R_3$ are independently selected from conjugated polyunsaturated fatty acids having from 16 carbon atoms to 22 carbon atoms, preferably conjugated linoleic acid, conjugated linolenic acid, and conjugated arachidonic acid, more preferably conjugated linoleic acid; and $R_2$ is selected from the group consisting of OH, $PO_3HR_4$, and $C_6$–$C_{12}$ carboxylic acids, wherein further $R_4$ is selected from the group consisting of OH, choline, inositol, serine, and ethanolamine.

The present invention also comprises methods of enhancing mouthfeel for oral compositions comprising adding said acylglycerol compounds to said oral compositions.

DETAILED DESCRIPTION OF THE INVENTION

The present invention comprises oral compositions, having enhanced organoleptic characteristics of fattiness, creaminess, soothing, satisfaction, and full mouthfeel, comprising a safe and effective amount of specific acylglycerol compounds, more specifically compounds comprising long chain conjugated polyunsaturated fatty acids. The present invention further comprises methods for enhancing the mouthfeel of oral compositions.

The term "acylglycerol", as used herein, is defined as compounds consisting of one or more of the same or different fatty acid residues, and/or phosphate containing residues, esterified to glycerol, 1,2,3-propanetriol, having the formula $(CH_2OH)_2CHOH$. The acylglycerol compounds of the present invention are more specifically defined as consisting of acylglycerol compounds comprising conjugated polyunsaturated fatty acid residues on the glycerol backbone at $R_1$, and/or $R_2$, and/or $R_3$ positions.

The term "conjugated polyunsaturated fatty acid residue", as used herein, is defined as fatty acid compounds, having 16 to 22 carbon atoms, and at least two double bonds, wherein said double bonds alternate with single bonds. Various positional and geometric isomers of conjugated polyunsaturated fatty acid residues involving the double bonds exist and are meant to be included herein. The conjugated polyunsaturated fatty acid residue octadecadienoic acid (18:2) is also known as conjugated linoleic acid (9-cis, 11-trans-octadecadienoic acid and/or 10-cis, 12-trans-octadecadienoic acid); octadecatrienoic acid (18:3) is also known as conjugated linolenic acid; and eicosatetraenoic acid (20:4) is also known as conjugated arachidonic acid. The above-described chemical and common names for these conjugated polyunsaturated fatty acid residues represent the same compounds and may be used interchangeably herein.

The phrase "oral compositions", as used herein, is defined as any foods and non-foods compositions which in the ordinary course of usage is placed in the oral cavity. Foods include compositions which are intentionally swallowed, such as natural and/or processed foods, premix and prepared drinks, candies, premix and prepared nutraceuticals, and the like. Non-foods include compositions which may be intentionally swallowed or not swallowed, as appropriate, such as over-the-counter and/or prescription pharmaceuticals, dental compositions, and the like. "Over-the-counter and/or prescription pharmaceuticals", as used herein, means any composition intentionally swallowed in the ordinary course of treating a specific ailment and/or disease symptom, such as chewable and swallowable tablets, capsules, granules, medicinal pills, powders, pellets, troches, liquids, extracts, elixirs, spirits, and syrups. "Dental compositions", as used herein, means any composition used in the oral cavity and/or to clean the teeth, and which is intentionally not swallowed but rather retained in the oral cavity for a time and then substantially expectorated, such as gums, dentifrices, mouthwashes, mouthrinses, and the like.

The term "dentifrice", as used herein, is defined as any composition, including toothpowders, toothpastes, toothgels, or liquids, which are generally used when brushing the teeth.

The phrase "safe and effective amount", as used herein, is defined as an amount of a substance sufficient to provide the desired benefit without undue adverse side effects, such as toxicity, irritation, or allergic response, commensurate with a reasonable benefit/risk ratio when used in the manner of this invention.

The term "compatible", as used herein, is defined as that the components of the compositions are capable of being co-mingled with one another without substantially reducing the efficacy of the components or the composition under ordinary use conditions.

The phrase "pharmaceutically-acceptable carrier materials", as used herein, means one or more compatible solid or liquid filler diluents or encapsulating substances which are suitable for oral and/or nasal administration to a human or lower animal. Pharmaceutically-acceptable carrier materials must, of course, be of sufficiently high purity and sufficiently low toxicity to render them suitable for administration to the human being treated.

The phrase "orally-acceptable carrier materials", as used herein, means any material safe and effective for use in the oral compositions of the present invention. Such materials include but are not limited to, thickening materials, humectants, water, buffering agents, abrasive polishing materials, sodium bicarbonate, titanium dioxide, surfactants, flavors, sweeteners, coloring agents, coolants, and mixtures thereof.

The acylglycerol compounds of the present invention, which when added to oral compositions provide a greater sense of fattiness, creaminess, satisfaction, soothing, and full mouthfeel to said oral compositions, have unique chemical structures. That is, $R_1$ and $R_2$ are independently selected from the group consisting of conjugated polyunsaturated fatty acids having from 16 carbon atoms to 22 carbon atoms, preferably conjugated linoleic acid, conjugated linolenic acid, and conjugated arachidonic acid, more preferably wherein at least one of $R_1$ and $R_2$ are conjugated linoleic acid, still more preferably wherein $R_1$ is conjugated linoleic acid and $R_2$ is selected from the group consisting of conjugated linoleic acid, conjugated linolenic acid, and conjugated arachidonic acid, most preferably wherein $R_1$ and $R_2$ are conjugated linoleic acid; and $R_3$ is selected from the group consisting of $R_1$, OH, $PO_3HR_4$, and $C_6$–$C_{12}$ carboxylic acids, preferably conjugated linoleic acid, OH, $PO_3HR_4$, and $C_6$–$C_{12}$ carboxylic acids, more preferably conjugated linoleic acid, OH, and $C_6$–$C_{12}$ carboxylic acids, most preferably conjugated linoleic acid and OH; wherein $R_4$ is selected from the group consisting of OH, choline, inositol, serine, and ethanolamine.

Some examples of conjugated polyunsaturated fatty acid residues include, but are not limited to, hexadecadienoic acid (16:2), hexadecatrienoic acid (16:3), hexadecatetraenoic acid (16:4), octadecadienoic acid (18:2), octadecatrienoic acid (18:3), octadecatetraenoic acid (18:4), eicosadienoic acid (20:2), eicosatetraenoic acid (20:4), eicosapentaenoic acid (20:5), docosapentaenoic acid (22:5), and docosahexaenoic acid (22:6).

Some examples of $C_6$–$C_{12}$ carboxylic acids include, but are not limited to, hexanoic/caproic acid (6:0), heptanoic acid (7:0), octanoic/caprylic acid (8:0), nonanoic acid (9:0), decanoic/capric acid (10:0), and dodecanoic/lauric acid (12:0).

In the alternative, the acylglycerol compounds may comprise those compounds wherein $R_1$ is selected from the group consisting of conjugated linoleic acid, conjugated linolenic acid, and conjugated arachidonic acid, $R_2$ is conjugated linoleic acid, and $R_3$ is selected from the group consisting of $R_1$, OH, $PO_3HR_4$, wherein $R_4$ is selected from the group consisting of OH, choline, inositol, serine, and ethanolamine, and $C_6$–$C_{12}$ carboxylic acids.

While purified fractions of the above-described acylglycerol compounds are preferred, a mixture of the above-described acylglycerol compounds have also been shown to achieve the desired organoleptic attributes of the present invention. That is, useful results have been shown using a mixture comprising about 50%, preferably greater than about 50%, more preferably greater than about 70%, most preferably greater than about 90% by weight, of acylglycerol compounds wherein $R_1$ and $R_2$ are independently selected from the group consisting of conjugated linoleic acid, conjugated linolenic acid, and conjugated arachidonic acid and $R_3$ is selected from the group consisting of OH and $C_6$–$C_{12}$ carboxylic acids, and about 50%, preferably less than about 50%, more preferably less than about 30%, most preferably less than about 10% by weight, of acylglycerol compounds wherein $R_1$, $R_2$, and $R_3$ are independently selected from the group consisting of conjugated linoleic acid, conjugated linolenic acid, and conjugated arachidonic acid.

In the alternative, the preferred mixtures may comprise greater than about 50%, more preferably greater than about 70%, most preferably greater than about 90% by weight, of acylglycerol compounds wherein $R_1$, $R_2$, and $R_3$ are independently selected from the group consisting of conjugated linoleic acid, conjugated linolenic acid, and conjugated arachidonic acid; and less than about 50%, more preferably less than about 30%, most preferably less than about 10% by weight, of acylglycerol compounds wherein $R_1$ and $R_2$ are independently selected from the group consisting of conjugated linoleic acid, conjugated linolenic acid, and conjugated arachidonic acid, and $R_3$ is selected from the group consisting of OH and $C_6$–$C_{12}$ carboxylic acids.

Other acylglycerol compounds useful in achieving the desired sensory attributes of the present invention may include, but are not limited to, those compounds wherein one of $R_1$ or $R_2$ or $R_3$ is the saturated fatty acid residue, palmitic acid (hexadecanoic acid), preferably wherein $R_1$ is selected from the group consisting of conjugated linoleic acid, conjugated linolenic acid, and conjugated arachidonic acid, more preferably wherein $R_1$ is conjugated linoleic acid, $R_2$ is palmitic acid, and $R_3$ is selected from the group consisting of $R_1$, OH, $PO_3HR_4$, wherein $R_4$ is selected from the group consisting of OH, choline, inositol, serine, and ethanolamine, and $C_6$–$C_{12}$ carboxylic acids.

Further acylglycerol compounds useful in achieving the desired sensory attributes of the present invention may include, but are not limited to, those compounds wherein $R_1$ and $R_3$ are independently selected from the group consisting of conjugated polyunsaturated fatty acids having from 16 carbon atoms to 22 carbon atoms and palmitic acid, preferably wherein at least one of $R_1$ and $R_3$ is selected from the group consisting of conjugated linoleic acid, conjugated linolenic acid, and conjugated arachidonic acid, more preferably wherein at least one of $R_1$ and $R_3$ is conjugated linoleic acid and $R_2$ is selected from the group consisting of OH, $PO_3HR_4$, wherein $R_4$ is selected from the group consisting of OH, choline, inositol, serine, and ethanolamine, and $C_6$–$C_{12}$ carboxylic acids.

The acylglycerol compounds of the present invention may be derived from any synthetic method or natural source, but are typically produced by the esterification of specific mixtures of fatty acids comprising the specific conjugated polyunsaturated fatty acid residues of interest with glycerine. This method is based on driving the reaction to completion by removing the water formed by the dehydration of the acid and alcohol residues to form the ester. Based on the progress of the reaction, the resulting product is usually a mixture of acylglycerols in addition to some residual fatty acids, glycerine and aroma compounds. The reaction mixture is then purified to isolate the various acylglycerol fractions. Other production methods for the acylglycerol compounds of the present invention may include the identification and isolation from natural or processed oil sources. Purification of the desired acylglycerols may proceed by a variety of methods including distillation, fractional crystallization, solvent extraction and chromatographic methods. Methods for these procedures are well known to those skilled in the art, however, examples may be found in *Bailey's Industrial Oil and Fat Products* (John Wiley & Sons, New York, 1982), which is incorporated herein by reference in its entirety.

The oral compositions described herein are substantially free of free conjugated polyunsaturated fatty acids and/or monoacylglycerol compounds, that is, less than about 10%, preferably less than about 1%, more preferably less than about 0.1%, and most preferably about 0%.

The amount of the acylglycerol compounds of the present invention to be added to the oral compositions depends on various factors such as the nature of the composition, the concentration therein of endogenous fat, the amount of exogenous fat which is acceptable, and the degree of enhanced mouthfeel desired. It has been found that a safe and effective amount of acylglycerol compounds of the present invention may comprise from about 0.001% to about 99% of the total oral composition. However, useful results have been obtained by adding from about 0.001% to about 70% by weight, preferably from about 0.001% to about 50% by weight, more preferably from about 0.001% to about 30% by weight, still more preferably from about 0.001% to about 10% by weight, most preferably from about 0.001% to about 1% by weight, and still most preferably an amount less than 1%, by weight of the acylglycerol compounds to the oral composition. It has also been found that when adding the acylglycerol compounds of the present invention to various liquid compositions, it is preferred to include the acylglycerol compounds in the form of an emulsion in water, wherein the ratio of acylglycerol compounds to emulsifier is about 1:1. The total amount of the acylglycerol compounds present in the final compositions however, should be within the limits described above.

While there are no specific limitations with respect to the oral compositions to which the acylglycerol compounds of the present invention may be added, the acylglycerol compounds of the present invention may be added to any conventional, reduced-fat, low-fat, and/or no-fat oral composition wherein the organoleptic attributes of fattiness, creaminess, satisfaction, soothing, and full mouthfeel are desired. Examples of such oral compositions include, but are not limited to, foods, drinks/beverages, confectioneries, nutraceuticals, dental compositions, over-the-counter and/or prescription pharmaceuticals, and the like.

Typically, the oral compositions described above are prepared simply by incorporating a safe and effective amount, as described above, of the acylglycerol compounds of the present invention therewith, as long as the acylglycerol compounds are compatible with the other components of the compositions. The foods, beverages, dental compositions, and over-the-counter and/or prescription pharmaceuticals may be prepared by any suitable method for making these compositions which is generally known in the art and may be readily chosen by one skilled in the art based on the physical and aesthetic properties desired for the composition being prepared.

Examples of foods to which the acylglycerol compounds of the present invention may be added include, but are not limited to, sauces; foods originating from soybeans; emulsion foods such as salad and sandwich dressings, whippable toppings, mayonnaises, margarines, margarine substitutes and blends; soups including powdery soups and prepared soups; dairy products such as butter, creams, puddings, yogurts, cheeses, cheese spreads, egg products and substitutes; frozen desserts such as frozen novelties, ice cream, sherbet, ices, regular and malted milk shakes; bakery items such as breads, biscuits, rolls, cakes, pastries, cookies, fillings, pie crusts, frostings; breakfast cereals; snack foods such as flavored dips, peanut butter, potato chips, corn chips, pop corn, pretzels, nuts, and crackers; confectioneries such as candies, chewing gum, and chocolate; frying fats and oils; vegetable and fruit products; meats and meat products, substitutes, and extenders; dry and canned pet foods; mixes and/or ingredient premixes of any of these; and the like.

Examples of drinks/beverages to which the acylglycerol compounds of the present invention may be added include, but are not limited to, prepared and frozen concentrate fruit juices; dilute juice beverages; vegetable juices; powdered drink mixes; milks such as whole and low-fat milks, flavored milks, powdered milks, condensed milks, and evaporated milks; cocoa; coffees and coffee products such as instant coffees, powdered and/or flavored coffees; dairy and non-dairy, liquid and dry, coffee lighteners; teas and tea products such as instant teas, powdered and/or flavored teas; sport drinks; carbonated drinks, refreshing drinks such as ades, alcoholic drinks such as beers, wines, and mixed drinks; and the like.

Examples of nutraceuticals to which the acylglycerol compounds of the present invention may be added include, but are not limited to, health foods; diet products; health drinks such as mixable and prepared protein drinks; chewable vitamins and mineral supplements; and the like.

Examples of dental compositions to which the acylglycerol compounds of the present invention may be added include, but are not limited to, gums, dentifrices, mouthwashes, mouthrinses, and the like. The dental compositions typically comprise at least one dental active and orally-acceptable carrier materials. The dental actives typically comprise a safe and effective amount of anticalculus agents, anticaries agents, antimicrobial/antiplaque agents, antibacterial agents, anti-inflammatory agents, surfactants, nutrients, and the like. Typical examples of anticalculus agents include, but are not limited to, those disclosed in U.S. Pat. No. 3,429,963, issued Feb. 25, 1969; U.S. Pat. No. 3,678,154, issued Jul. 18, 1972; U.S. Pat. No. 3,737,533, issued Jun. 5, 1973; U.S. Pat. No. 3,988,443, issued Oct. 26, 1976; U.S. Pat. No. 4,304,766, issued Dec. 8, 1981; U.S. Pat. No. 4,515,772, issued May 7, 1985; U.S. Pat. No. 4,590,066, issued May 20, 1986; U.S. Pat. No. 4,661,341, issued Apr. 28, 1987; U.S. Pat. No. 4,846,650, issued Jul. 11, 1989; U.S. Pat. No. 4,877,603, issued Oct. 31, 1989; U.S. Pat. No. 5,068,100, issued Nov. 26, 1991; U.S. Pat. No. 5,096,701, issued Mar. 17, 1992; U.S. Pat. No. 5,338,537, issued Aug. 16, 1994; all of these patents are incorporated herein, in their entirety by reference.

Typical examples of anticaries agents include, but are not limited to, a water-soluble fluoride ion source such as sodium fluoride, potassium fluoride, indium fluoride, stannous fluoride, and sodium monofluorophosphate, which are disclosed in U.S. Pat. No. 2,946,735, issued Jul. 26, 1960; U.S. Pat. No. 3,535,421, issued Oct. 20, 1970; and U.S. Pat. No. 3,678,154, issued Jul. 18, 1972; all of which are incorporated herein, in their entirety by reference.

Typical examples of antimicrobial/antiplaque agents include, but are not limited to, those described in *The Merck Index*, 10th ed. (1976); U.S. Pat. No. 3,506,720, issued Apr. 14, 1970; U.S. Pat. No. 4,022,880, issued May 10, 1977; U.S. Pat. No. 4,574,081, issued Mar. 4, 1986; U.S. Pat. No. 4,670,252, issued Jun. 2, 1987; European Patent Application 0,251,591, published Jan. 7, 1988; U.S. Pat. No. 5,004,597, issued Apr. 2, 1991; U.S. Pat. No. 5,188,820, issued Feb. 23, 1993; U.S. Pat. No. 5,338,537, issued Aug. 8. 1994; U.S. Pat. No. 5,389,360, issued Feb. 14, 1995; and U.S. Pat. No. 5,389,360, issued Feb. 14, 1995; all of which are incorporated herein, in their entirety by reference.

Typical examples of antibacterial agents include, but are not limited to, cationic and/or noncationic, which may be substantially water soluble or insoluble, antibacterial agents such as cetylpyridinium chloride (CPC) and Triclosan, as disclosed by U.S. Pat. No. 3,431,208, issued Mar. 4, 1969; U.S. Pat. No. 3,703,583, issued Nov. 21, 1972; British Patent 1,319,396, issued Jun. 6, 1973; British Patent 2,200,551, issued Aug. 10, 1988; and European Patent Application 0,528,468, published Feb. 24, 1993; all of which are incorporated herein, in their entirety by reference.

Typical examples of anti-inflammatory agents include, but are not limited to, aspirin, ibuprofen, naproxen, indomethacin, piroxicam, flurbiprofen, meclofenamate sodium, ketoprofen, tenidap, tebufelone, ketorolac, and the like, as disclosed by British Patent 1,550,139, issued Aug. 8, 1979; and U.S. Pat. No. 5,459,135, Issued Oct. 17, 1995; both of which are incorporated herein, in their entirety by reference.

Typical examples of surfactants include, but are not limited to, those surfactants which are useful as sudsing agents and may be soaps, anionic, nonionic, cationic, zwitterionic and amphoteric organic synthetic detergents, and compatible mixtures thereof Surfactants of these types are described more fully in U.S. Pat. No. 3,959,458 issued May 25, 1976; and U.S. Pat. No. 4,051,234, issued Sep. 27, 1988; incorporated herein, in their entirety by reference.

Typical examples of nutrients include, but are not limited to, folate, retinoids (Vitamin A), Vitamin C, Vitamin E and zinc.

One or more orally-acceptable carrier materials may also be added to the dental compositions. Such materials are well known in the art and may be readily chosen by one skilled in the art based on the physical and aesthetic properties desired for the composition being prepared. Examples of typical orally-acceptable carrier materials include, but are not limited to, thickening materials, binders, humectants, titanium dioxide, flavoring agents, cooling agents, sweetening agents, buffering agents, and abrasive polishing materials, such as disclosed in U.S. Pat. No. 3,070,510, issued Dec. 25, 1962; U.S. Pat. No. 3,538,230, issued Mar. 2, 1970; U.S. Pat. No. 3,862,307, issued Jun. 21, 1975; U.S. Pat. No. 4,032,661, issued Jun. 28, 1977; U.S. Pat. No. 4,136,163, issued Jan. 23, 1979; U.S. Pat. No. 4,230,688, issued Oct. 28, 1980; U.S. Pat. No. 4,340,583, issued Jul. 29, 1982; U.S. Pat. No. 4,459,425, issued Jul. 10, 1984; and U.S. Pat. No. 5,266,592, issued Nov. 30, 1993; all of which are incorporated herein, in their entirety by reference.

The dental compositions of the present invention may also contain sodium bicarbonate, solubilizing agents suitable for solubilizing the anticalculus agents, anticaries agents, antimicrobial/antiplaque agents, antibacterial agents, anti-inflammatory agents, hydrogen peroxide, and water which is preferably deionized and free of organic impurities.

The dental compositions of the present invention can be in the form of a mouth rinse or liquid dentifrice where conventional mouth rinse components comprise the carrier materials of the present invention. Mouth rinses and liquid dentifrices generally comprise from about 20:1 to about 2:1 of a water ethyl alcohol or alcohol free solution, and preferably other ingredients such as flavors, sweeteners, humectants, and surfactants such as those mentioned above.

Examples of over-the-counter and/or prescription pharmaceutical compositions to which the acylglycerol compounds of the present invention may be added include, but are not limited to, cough/cold oral compositions, compositions for treating the oral cavity, and compositions for treating gastrointestinal distress. While there are no specific limitations with respect to the orally administrable pharmaceutical actives which may be used in these compositions, the pharmaceutically acceptable actives should be compatible with the acylglycerol compounds of the present invention, as well as other essential ingredients in the oral compositions.

Examples of cough/cold oral compositions typically comprise a safe and effective amount of at least one pharmaceutical active and pharmaceutically-acceptable carrier materials suitable for oral administration. Suitable pharmaceutically acceptable active materials or compounds useful for treating cough, cold, cold-like, allergy and/or flu symptoms are well known, and may be selected from, but are not limited to, an active having analgesic, anti-inflammatory, antipyretic, anesthetic, antihistamine, bronchodilators, decongestant, cough suppressant, demulcents, antitussive, and/or expectorant properties. Typical examples of decongestants include, but are not limited to, pseudoephedrine, phenylpropanolamine, phenylephrine and ephedrine, their pharmaceutically acceptable salts, antitussives include, but are not limited to, dextromethorphan, chlopedianol, carbetapentane, caramiphen, noscapine, diphenhydramine, codeine, hydrocodone, hydromorphone, their pharmaceutically acceptable salts, expectorants (also known as mucolytic agents) include, but are not limited to, guaifenesin, terpin hydrate, ammonium chloride, N-acetylcysteine, and ambroxol, their pharmaceutically acceptable salts, analgesics include, but are not limited to, morphine, codeine, meperidine, pentazocine, propoxyphene, acetaminophen, allopurinol, acetylsalicylic acid, choline salicylate, ketoprofen, magnesium silicate, fenoprofen, ibuprofen, flurbiprofen, indomethacin, naproxen, and many others, their pharmaceutically acceptable salts, antihistamines include, but are not limited to, brompheniramine, chlorpheniramine, clemastine, dexchlorpheniramine, diphenhydramine, doxylamine, promethazine, terfenadine, triprolidine, and many others, their pharmaceutically acceptable salts, and mixtures thereof.

These actives, as well as their acceptable dosage ranges are described in U.S. Pat. No. 4,522,828, issued Jun. 11, 1985; U.S. Pat. No. 4,619,934, issued Oct. 28, 1986; U.S. Pat. No. 4,783,465, issued Nov. 8, 1988; and Remington's Pharmaceutical Sciences, pp. 734–789, 791–799, 861–868, 907–945, 875–888, 1002–1034, 1098–1121, 1124–1131, 1173–1224, 1232–1241 (Alfonso R. Gennaro, editor) (18th ed. 1990), all of which are incorporated herein, in their entirety by reference.

The choice of pharmaceutically-acceptable carrier materials to be used in conjunction with the pharmaceutical cold active of the present compositions is basically determined by the dose form for the compositions and are well known in the art. Pharmaceutically-acceptable carrier materials and excipients suitable for the preparation of dosage forms for oral administration are described in U.S. Pat. No. 3,903,297, issued Sep. 2, 1975, incorporated herein, in its entirety by reference.

Other optional ingredients well known to the pharmacist's art may also be included in amounts generally known for these ingredients, such as a cooling agent or a combination of cooling agents and/or caffeine. Suitable cooling agents include, but are not limited to, 3-1-menthoxy propane 1,2-diol, N-substituted-p-menthane-3-carboxamides, and acyclic carboxamides, which are described in U.S. Pat. No. 4,032,661, issued Jun. 28, 1977; U.S. Pat. No. 4,136,163, issued Jan. 23, 1979; U.S. Pat. No. 4,230,688, issued Oct. 28, 1980; U.S. Pat. No. 4,459,425, Jul. 10, 1984; and U.S. Pat. No. 5,266,592, issued Nov. 30, 1993; all of which are incorporated herein, in their entirety by reference.

Examples of compositions for treating gastrointestinal distress typically comprise a safe and effective amount of at least one pharmaceutical agent useful for treating upper gastrointestinal tract distress and pharmaceutically-acceptable carrier material suitable for oral administration. Pharmaceutical actives useful for treating upper gastrointestinal tract distress are those materials which are safe and effective when administered orally for treating disorders of the upper gastrointestinal tract (typically the stomach and/or esophagus) which result in symptoms of upper gastrointestinal tract distress (e.g., heartburn, stomachache, indigestion). Typical actives may include, but are not limited to, antacid agents and acid secretion prevention agents (e.g., H2 receptor-blocking anti-secretory agents), such as those disclosed in U.S. Pat. No. 5,128,140, issued Jul. 7, 1992 and U.S. Pat. No. 5,244,670, issued Sep. 14, 1993, both of which are incorporated herein, in their entirety by reference. Examples include antacid agents such as aluminum carbonate, aluminum hydroxide, aluminum phosphate, aluminum hydroxy-carbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumino silicates, magnesium carbonate, magnesium glycinate, magnesium hydroxide, magnesium oxide, magnesium trisilicate, sucralfate; acid secretion prevention agents such as cimetidine, ranitidine, famotidine, omeprazole; bismuth-containing agents such as bismuth subsalicylate, bismuth aluminate, bismuth citrate, bismuth subcitrate, bismuth nitrate, bismuth subcarbonate, bismuth subgalate; anticholinergics such as atropine, clidinium and dicyclomine; laxatives such as phenolphthalein and casanthrol; and antidiarrheals such as diphenoxylate and loperamide.

The choice of pharmaceutically-acceptable carrier and excipient materials used in conjunction with the pharmaceutical active useful for treating upper gastrointestinal tract distress is basically determined by the dose form for the compositions and are well known in the art. Their selection will depend on secondary considerations like taste, cost, shelf stability, which are not critical for the purposes of the present invention, and can be made without difficulty by a person skilled in the art.

The pharmaceutically-acceptable carrier materials employed in the present ingestible compositions are used at concentrations sufficient to provide a practical size to dosage relationship. Some examples, such as those disclosed in U.S. Pat. No. 5,128,140, issued Jul. 7, 1992 and U.S. Pat. No. 5,244,670, issued Sep. 14, 1993, both of which are incorporated herein, in their entirety by reference, include, but are not limited to, sugars such as lactose, glucose and sucrose; starches such as corn-starch and potato starch; cellulose and its derivatives such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobroma; polyols such as propylene glycol, glycerine, sorbitol, mannitol, and polyethylene glycol; agar; alginic acid; wetting agents and lubricants such as sodium lauryl sulfate; coloring agents; flavoring agents; sweetening agents (including nonnutritive sweeteners such as aspartame and saccharin); tableting agents; stabilizers; antioxidants; cooling agents such as those described above; preservatives; caffeine; and the like. Other compatible pharmaceutical additives and actives which are not typical pharmaceutical actives useful for treating upper gastrointestinal tract distress (e.g., NSAID drugs; pain killers; muscle relaxants) may also be included in the compositions of the present invention.

The over-the-counter and/or prescription pharmaceutical compositions can be in any dosage form including, but not limited to, solid preparations such as chewable and swallowable tablets, capsules, granules, medicinal pills, powders, pellets, troches and dry syrups; and liquid preparations such as liquids, extracts, elixirs, spirits, syrups, aromatic water, lemonades, and fluid-extracts. The preferred dosage forms are liquid solutions, liquid suspensions, chewable and/or swallowable tablets, capsules and the like.

The acylglycerol compounds may be incorporated into the dental compositions, and over-the-counter and/or prescription pharmaceutical compositions described above in any conventional manner. For instance, the acylglycerol compounds may be incorporated into the compositions singly or in combination with one or more known additives, such diluents, fillers, binders, disintegrators, lubricants, fluidity-improving agents, coating agents, flavors, masking agents, perfumes, and anti-oxidation agents.

The acylglycerol compounds may also be coated on a composition. For instance, foods in the form of a solid, such as candy, other confectioneries, processed fish/meats, vegetables, fruits, processed vegetables, processed fruits, dried vegetable juices, and dried fruits juices and pharmaceutical preparations in the form of powder, granules, pellets, tablets, soft and hard capsules, and pills. The coating layer can comprise the acylglycerol compounds and hydrophilic polymers such as cellulose derivatives, gelatin, and polyvinyl alcohol. Other additives such as sweeteners and flavors can be incorporated into the coating layer. There is no need of coating the whole surface of the material. Partial coating may also be employed. The coating comprising the acylglycerol compounds may be made on the composition which already contains the acylglycerol compounds. For the coating, any known coating methods and coating apparatuses can be used.

EXAMPLES

The following examples further describe and demonstrate embodiments within the scope of the present invention. These examples are given solely for the purpose of illustration and are not to be construed as a limitation of the present invention as many variations thereof are possible without departing from the spirit and scope of the present invention.

Example 1

A beverage is prepared by mixing the following ingredients.

| Ingredient | Weight Percent |
| --- | --- |
| Guar gum | 0.02 |
| Xanthan | 0.04 |
| Propylene glycol alginate | 0.075 |
| Sugar | 15.0 |
| Fruit Juice Concentrate | 1.47 |
| Peel Oil | 0.03 |
| Cotton seed oil | 0.10 |
| Acylglycerol | 0.10 |
| Water | Q.S. |

The beverage is made by mixing the guar gum, xanthan, and propylene glycol alginate, with about 10% of the water under high shear. The remained of ingredients are added with the water/thickener system under low shear.

Example 2

A flavored instant coffee product is prepared by blending, in a ribbon blender, about 51% by weight, of a commercial grade non-dairy creamer and about 49% by weight, of a fine grade sugar for 5 minutes. The resultant mixture is agglomerated with steam, as disclosed in U.S. Pat. No. 3,652,293, issued Mar. 28, 1972, and fed onto a vibrating feeder, wherein the agglomerate falls onto a forming plate having multiple fluted channels. The agglomerate is exposed to a jet of steam, having a velocity of about 500 ft/min. and discharged onto a moving belt which allows the agglomerates to set for about 70 seconds before being dried at 74° C. for 60 seconds. About 84.8% by weight, of the dried agglomerate is blended with about 5% spray dried soluble coffee (ground to about less than 200 mesh), about 10% dutched lecithinated cocoa solids (10–12% fat and ground to about less than 200 mesh), about 0.01% acylglycerol, and about 0.1% flavors, until the agglomerate is coated with the flavor base components

Example 3

A low-calorie fabricated potato chip is prepared by mixing about 58.5% potato flour, 40.5% water, and 1.0% emulsifier (blend of mono- and diglycerides) for two minutes in a domestic food processor to yield a loose, dry dough. The dough is sheeted by feeding it through a pair of commercial 20 cm mill rolls to form a smooth elastic sheet of about 0.05 cm thick. The dough sheet is then cut into oval shaped pieces and placed into a constrained cooking mold consisting of 6 pair of perforated stainless steel halves. The molds are then passed through a continuous fryer filled with about 98% cottonseed olestra (Olean®, The Procter & Gamble Co., Cincinnati, Ohio) and about 2% acylglycerol at 190° C. for a time sufficient to lower the moisture content to about 1.0–2.0% (about 10–15 seconds). The mold apparatus is removed from the oil and the finished chips, containing about 34.3% olestra and about 0.7% acylglycerol, are removed from the molds, cooled to room temperature, salted, and packaged.

Example 4

An oven-baked French fry is prepared by peeling and cutting Russet Burbank potatoes into 0.64 cm square strips. The strips are then blanched in hot (about 77° C.) water for 7 minutes, then partially air dried in a convection oven at about 80° C. for 10 minutes. The strips are then fried in about 90% Primax 108 vegetable oil (blend of partially hydrogenated soybean oil and corn oil available from The Procter & Gamble Co., Cincinnati, Ohio) and about 10% acylglycerol at about 182° C. for about 2 minutes to reduce the moisture content to about 58%. The parfried strips are then frozen in a blast freezer (about 10 minutes at about −40° C.) and stored at about −18° C. The frozen parfries are prepared for consumption by baking in a conventional home oven at about 232° C. for about 15–20 minutes. The finished oven-baked French fries contain about 7.2% fat and about 0.8% acylglycerol.

Example 5

A baked cake product is prepared as follows.

| Ingredient | Weight Percent |
| --- | --- |
| Cake flour | 36.90 |
| Sugar | 43.20 |
| Shortening | 10.50 |
| Leavening[1] | 2.50 |
| Acylglycerol | 0.90 |
| Conventional additives[2] | 6.00 |

[1]The leavening comprises a baking soda, for example sodium, potassium, or ammonium bicarbonate, and a baking acid, preferably sodium aluminum phosphate, monocalcium phosphate and dicalcium phosphate or mixtures thereof.
[2]The term "conventional cake additives" includes ingredients such as flavors, thickeners, nutrients, antioxidants, and antimicrobial agents, non-fat milk solids, egg solids, and whey proteins.

The above ingredients are blended into a dry premix by conventional blending techniques. A baked cake product is prepared by mixing about 520 grams of the premix, about 140 grams of egg, about 300 grams of water, and about 82 grams of oil to in a mixing bowl at medium speed for about 3 minutes. Mixing is continued at low speed for about 3 minutes or until the batter is a smooth homogenous blend. The batter is transferred to a cake pan and baked in a conventional home oven at about 165° C.–190° C. until done. The finished baked cake product contains about 0.6% acylglycerol.

Example 6

Given below is a dentifrice example representative of the present invention.

| Component | Weight % |
| --- | --- |
| Sorbitol (70% Solution) | 61.827 |
| Glycine | 0.218 |
| Sodium Fluoride | 0.243 |
| Sodium Alkyl Sulfate (28% Solution) | 4.000 |
| Saccharin | 0.130 |
| Titanium Dioxide | 0.525 |
| FD&C Blue | 0.050 |
| Silica | 20.000 |
| Xanthan Gum | 0.475 |
| Carbopol 956[1] | 0.300 |
| Acylglycerol | 2.000 |
| Flavor | 0.900 |
| Water | QS |

[1]Carboxyvinyl polymer offered by B. F. Goodrich Company.

Example 7

Given below is a mouthrinse example representative of the present invention.

| Component | Weight % |
| --- | --- |
| Ethanol | 12.000 |
| Glycerin | 10.000 |
| Dibasic Sodium Phosphate, Heptahydrate | 0.070 |
| Saccharin Sodium | 0.080 |
| Monobasic Sodium Phosphate, Monohydrate | 2.030 |
| Polysorbate 80 | 0.330 |
| Acylglycerol[1] | 0.376 |
| FD&C Blue (1% Soln) | 0.020 |
| Flavor | 0.150 |
| Purified Water | QS |

[1]Acylglycerol compound added as a 1:1 emulsion with modified food starch dissolved in water.

Example 8

Given below is a liquid cough/cold compositions for oral administration example representative of the present invention.

| Ingredient | % W/V |
| --- | --- |
| Acetaminophen | 1.00 |
| Dextromethorphan HBr | 0.15 |
| Chlorpheniramine Maleate | 0.02 |
| Pseudoephedrine HCl | 0.30 |
| Alcohol (95%) | 25.00 |
| Propylene Glycol | 25.00 |
| Sodium Citrate | 2.00 |

-continued

| Ingredient | % W/V |
| --- | --- |
| Citric Acid | 0.25 |
| Liquid Sugar (Simple Syrup) | 25.00 |
| Glycerin | 7.00 |
| Acylglycerol[1] | 2.000 |
| Colorants | 0.008 |
| Flavor | 0.50 |
| Water, Purified | QS |

[1]Acylglycerol compounds added as a 1:1 emulsion with modified food starch dissolved in water.

Example 9

Given below is a chewable ingestible tablet pharmaceutical composition example representative of the present invention.

| Ingredients | Weight % |
| --- | --- |
| Granulated calcium carbonate[1] | 42.87% |
| Magnesium stearate | 2.50% |
| Colored speckles | 0.75% |
| Flavorants | 0.78% |
| MPD[2] | 0.07% |
| WS-3[3] | 0.05% |
| Acylglycerol | 4.000% |
| Aspartame | 0.198% |
| Sodium Saccharin | 0.102% |
| Mannitol[4] | QS |

[1]Granulated calcium carbonate containing 93.3% calcium carbonate, 6.3% glucose and 0.4% gelatin; supplied by Whittaker Clark & Daniels, Philadelphia, Pa.
[2]3-1-menthoxy propane-1,2-diol, supplied by Takasago Perfumery Co., Ltd., Tokyo, Japan.
[3]N-ethyl-p-menthane-3-carboxamide, supplied by Sterling Drugs.
[4]Granulate mannitol supplied by ICI Americas, Inc., Wilmington, Delaware.

What is claimed is:

1. A method of enhancing the mouthfeel of an oral composition comprising the addition of acylglycerol compounds to said oral compositions, wherein said acylglycerol compounds comprise substituents $R_1$, $R_2$, and $R_3$ attached at the positions of the $OH^-$ groups of a glycerol backbone; said substituents $R_1$ and $R_2$ are independently selected from conjugated polyunsaturated fatty acids having from 16 carbon atoms to 22 carbon atoms and substituent $R_3$ is selected from the group consisting of $R_1$, $OH^-$, $PO_3HR_4$, and $C_6$–$C_{12}$, carboxylic acids, wherein $R_4$ is selected from the group consisting of $OH^-$, choline, inositol, serine, and ethanolamine; and wherein further said oral composition is substantially free of free conjugated polyunsaturated fatty acids.

2. A method of enhancing the mouthfeel of an oral composition according to claim 1, wherein said acylglycerol compounds comprise:
   a) about 50% of acylglycerol compounds wherein $R_1$ and $R_2$ are independently selected from the group consisting of conjugated linoleic acid, conjugated linolenic acid, and conjugated arachidonic acid, and $R_3$ is $OH^-$; and
   b) about 50% of acylglycerol compounds wherein $R_1$, $R_2$, and $R_3$ are independently selected from the group consisting of conjugated linoleic acid, conjugated linolenic acid, conjugated arachidonic acid, and $C_6$–$C_{12}$ carboxylic acids.

3. A method of enhancing the mouthfeel of an oral composition according to claim 1, wherein said acylglycerol compounds comprise:
   a) greater than 50% of acylglycerol compounds wherein $R_1$ and $R_2$ are independently selected from the group consisting of conjugated linoleic acid, conjugated linolenic acid, and conjugated arachidonic acid, and $R_3$ is $OH^-$; and
   b) less than 50% of acylglycerol compounds wherein $R_1$, $R_2$, and $R_3$ are independently selected from the group consisting of conjugated linoleic acid, conjugated linolenic acid, conjugated arachidonic acid, and $C_6$–$C_{12}$ carboxylic acids.

4. A method of enhancing the mouthfeel of an oral composition according to claim 1, wherein said acylglycerol compounds comprise:
   a) less than 50% of acylglycerol compounds wherein $R_1$ and $R_2$ are independently selected from the group consisting of conjugated linoleic acid, conjugated linolenic acid, and conjugated arachidonic acid, and $R_3$ is $OH^-$; and
   b) greater than 50% of acylglycerol compounds wherein $R_1$, $R_2$, and $R_3$ are independently selected from the group consisting of conjugated linoleic acid, conjugated linolenic acid, conjugated arachidonic acid, and $C_6$–$C_{12}$ carboxylic acids.

5. A method of enhancing the mouthfeel of an oral composition according to claim 1, wherein at least one of said substituents $R_1$ and $R_2$ is palmitic acid.

6. A method of enhancing the mouthfeel of an oral composition comprising the addition of acylglycerol compounds to said oral compositions, wherein said acylglycerol compounds comprise substituents $R_1$, $R_2$, and $R_3$ attached at the positions of the $OH^-$ groups of a glycerol backbone; said substituents $R_1$ and $R_3$ are independently selected from conjugated polyunsaturated fatty acids having from 16 carbon atoms to 22 carbon atoms and substituent $R_2$ is selected from the group consisting of $OH^-$, $PO_3HR_4$, and $C_6$–$C_{12}$ carboxylic acids, wherein $R_4$ is selected from the group consisting of $OH^-$, choline, inositol, serine, and ethanolamine; and wherein further said oral composition is substantially free of free conjugated polyunsaturated fatty acids.

* * * * *